(12) United States Patent
Jang et al.

(10) Patent No.: US 7,060,873 B2
(45) Date of Patent: Jun. 13, 2006

(54) METHOD FOR PRODUCING A PLANT WITH A HIGH-GROWTH RATE

(75) Inventors: In-Cheol Jang, Kyungki (KR); Yoon-Mok Park, Seoul (KR); Sang-Ik Song, Kyungki (KR); Ju-Kon Kim, Kyungki (KR); Baek-Hie Nahm, Kyungki (KR)

(73) Assignee: Greengene Biotech Inc., Kunggi-Do (KR)

( * ) Notice: Subject to any disclaimer, the term of this patent is extended or adjusted under 35 U.S.C. 154(b) by 341 days.

(21) Appl. No.: 10/321,732

(22) Filed: Dec. 18, 2002

(65) Prior Publication Data
US 2004/0123348 A1  Jun. 24, 2004

(30) Foreign Application Priority Data
Sep. 5, 2002  (KR) ..................... 10-2002-0053637

(51) Int. Cl.
*C12N 15/29* (2006.01)
*C12N 15/82* (2006.01)

(52) U.S. Cl. .................. 800/290; 800/278; 800/320.1; 536/23.6

(58) Field of Classification Search ............... 536/23.1, 536/23.6; 800/278, 290, 320, 298; 435/468
See application file for complete search history.

(56) References Cited

U.S. PATENT DOCUMENTS 6,287,843 B1 * 9/2001 Baldwin et al. ......... 435/252.3

OTHER PUBLICATIONS

Merriam Webster Online Dictionary (2005, www.m-w.com/home.html).*

* cited by examiner

*Primary Examiner*—David T. Fox
*Assistant Examiner*—Stuart F. Baum
(74) *Attorney, Agent, or Firm*—Nath & Associates PLLC; Harold L. Novick

(57) ABSTRACT

The present invention relates to proteins, OsHDAC1, OsHDAC2 and OsHDAC3, which function as histone deacetylase, a gene coding for said proteins, and a method for producing a plant having a high growth rate by expressing said gene in the plant. According to the present invention, the OsHDACs proteins change the structure of chromatin to increase or decrease the expression of a foreign gene in the genomes, so that the expression amount of the OsHDACs proteins can be controlled to produce a plant having varied phenotypic characteristics. Particularly, the OsHDAC1 protein is expressed locally in the plant and increases the growth rate of plant by its overexpression and its expression is increased by ABA. Therefore, this protein can be very efficiently used for producing plants having a high growth rate even under stress conditions including drought, cold, etc., as well as under normal conditions.

7 Claims, 6 Drawing Sheets

[Figure 1]
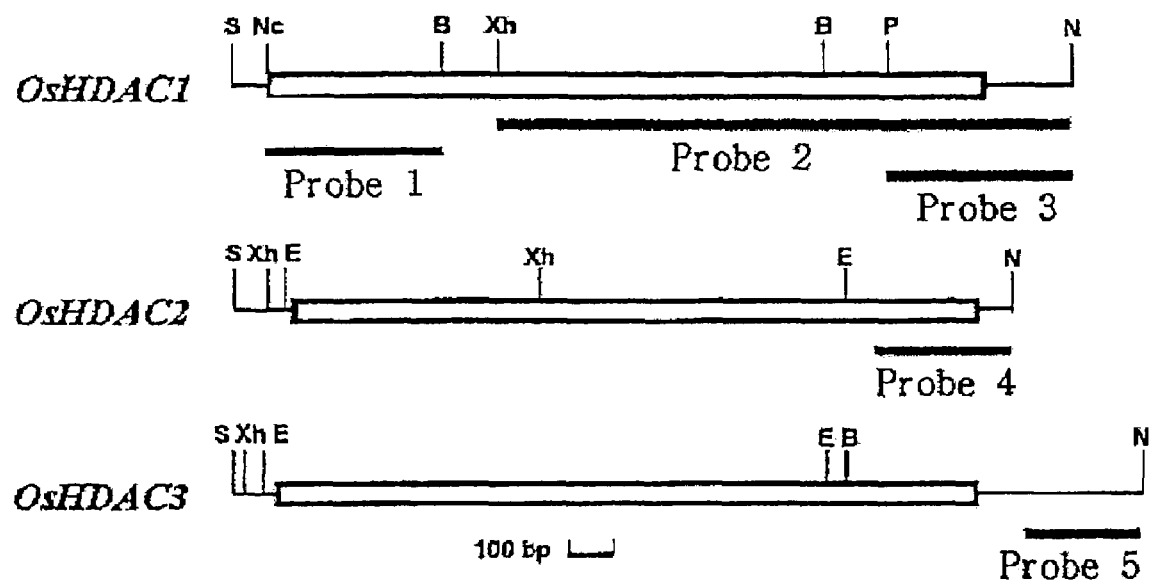
[Figure 2]
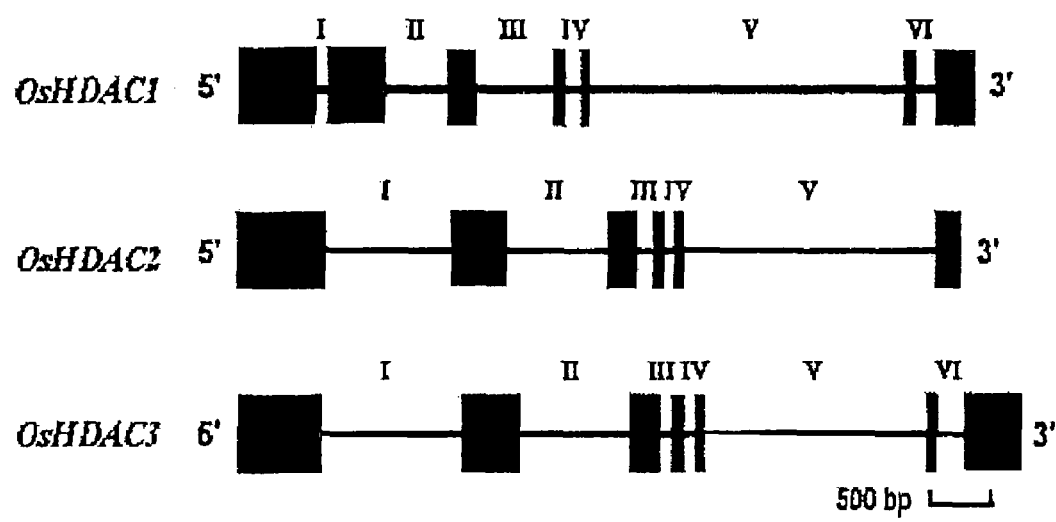

[Figure 3]
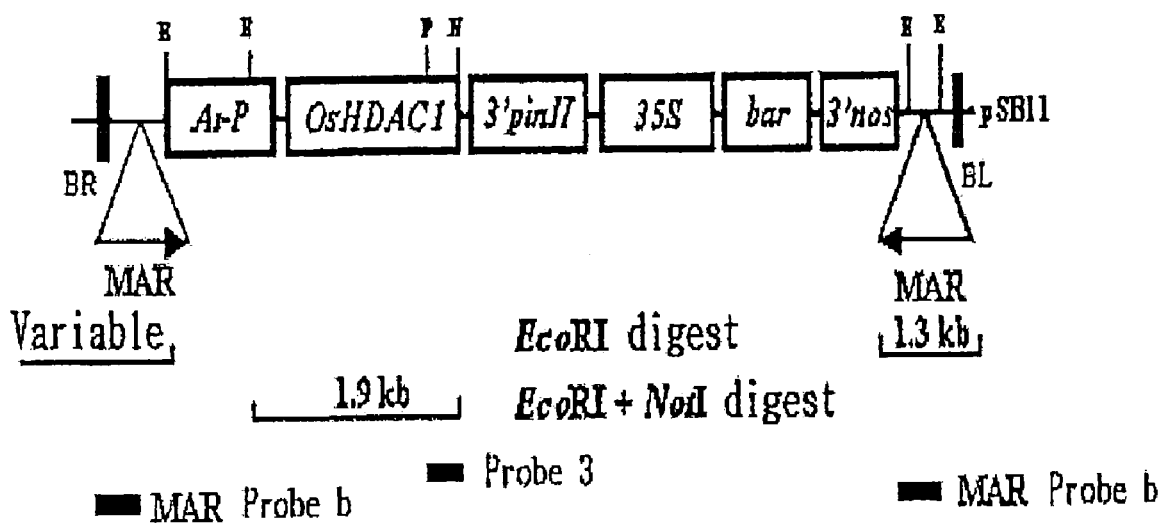
[Figure 4]
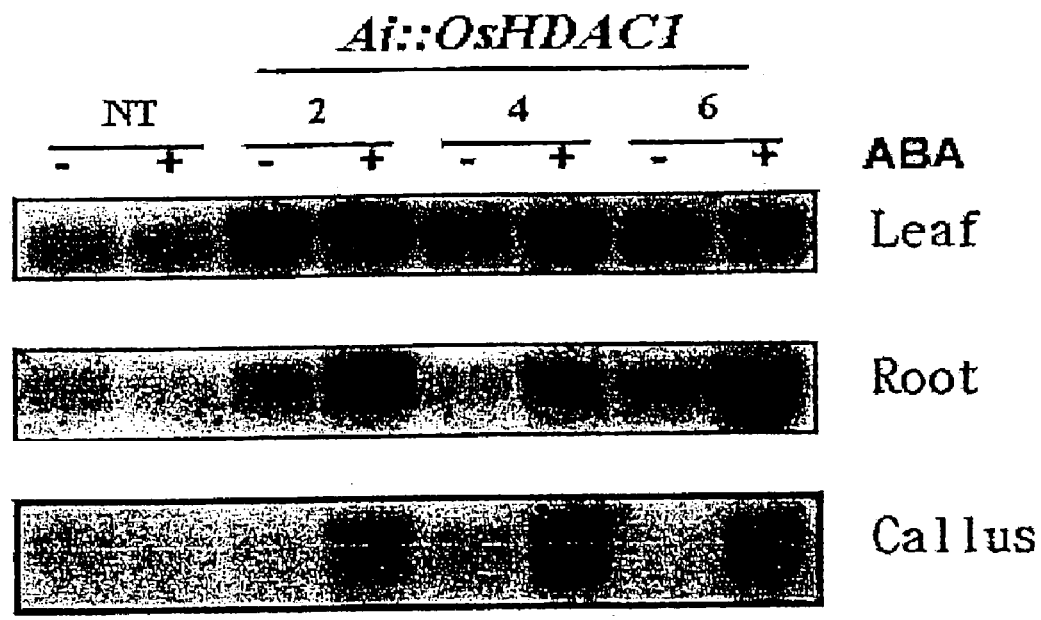

[Figure 5]
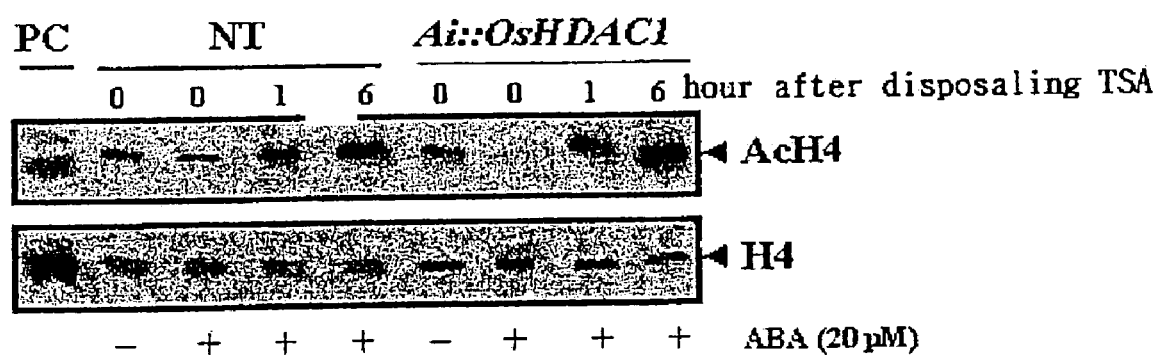
[Figure 6a]
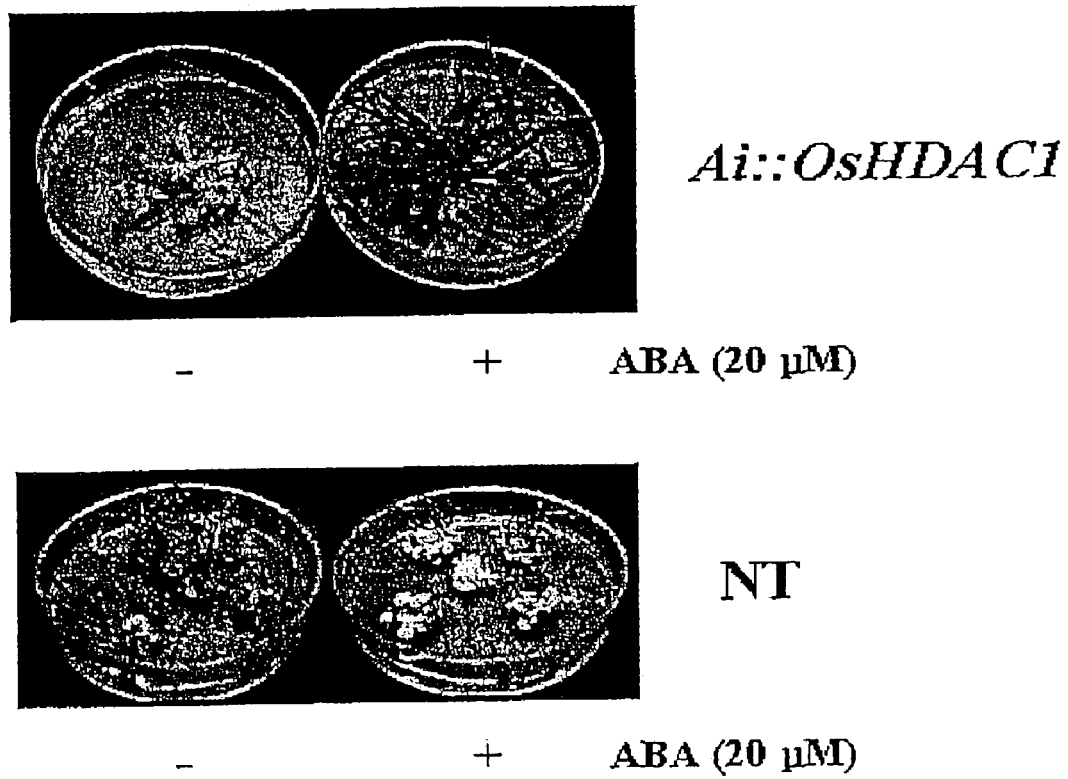

[Figure 6b]
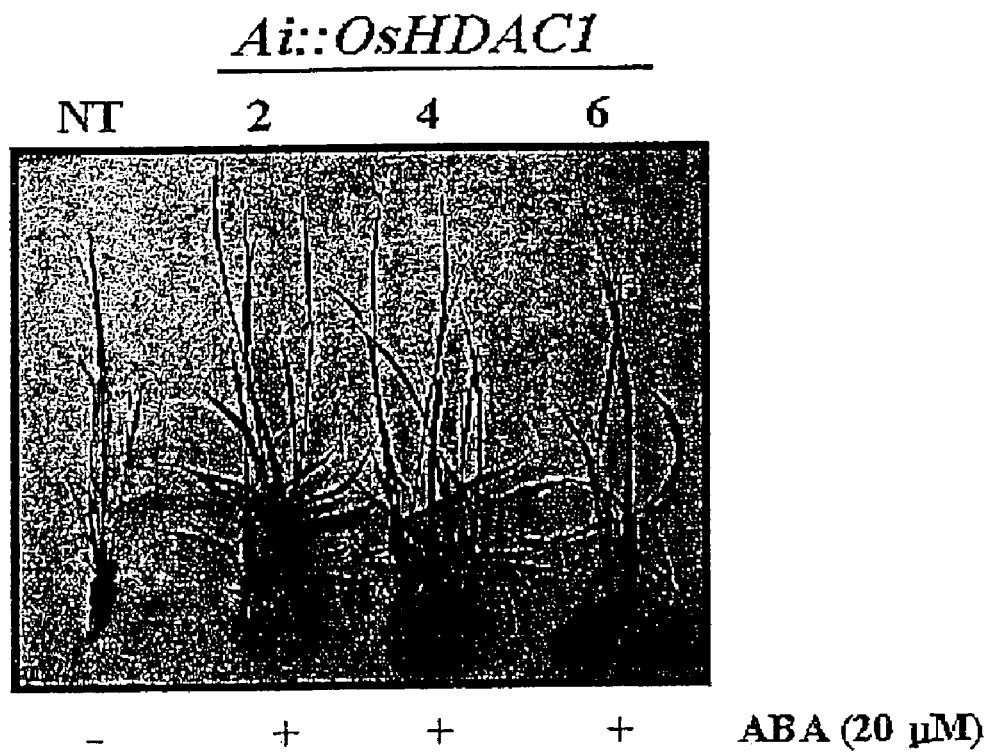
[Figure 6c]
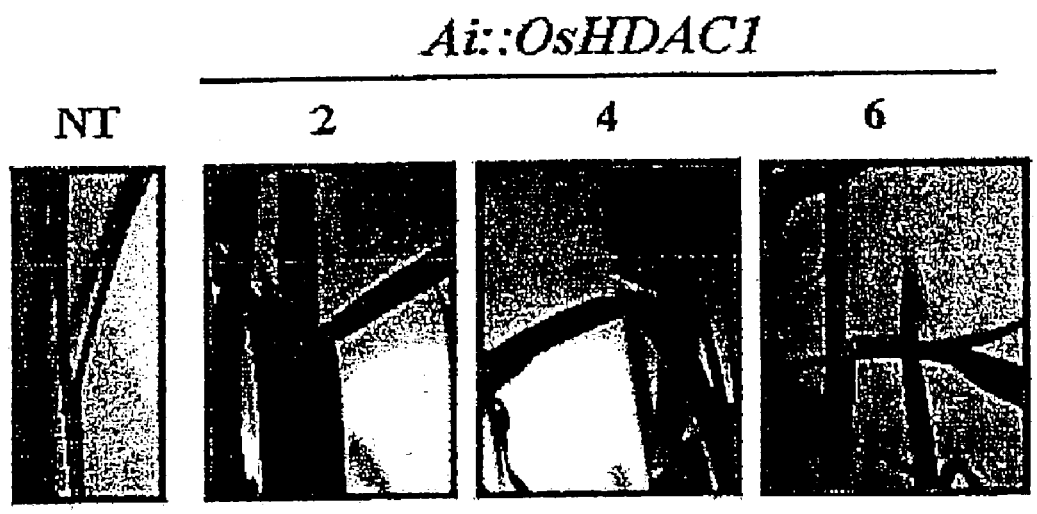

[Figure 6d]
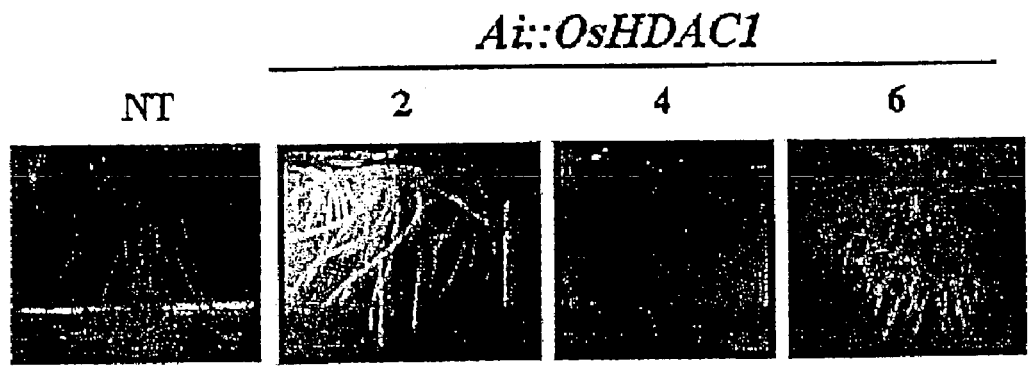
[Figure 7a]
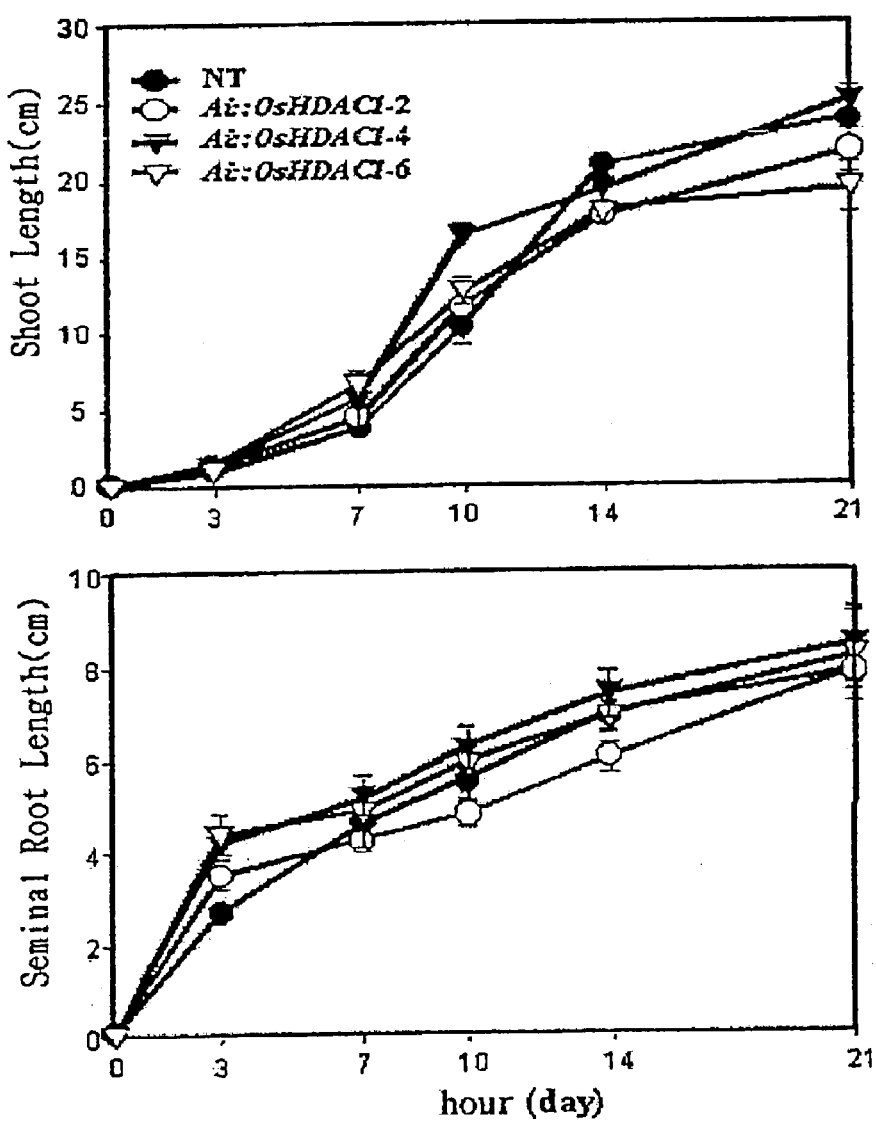

[Figure 7b]
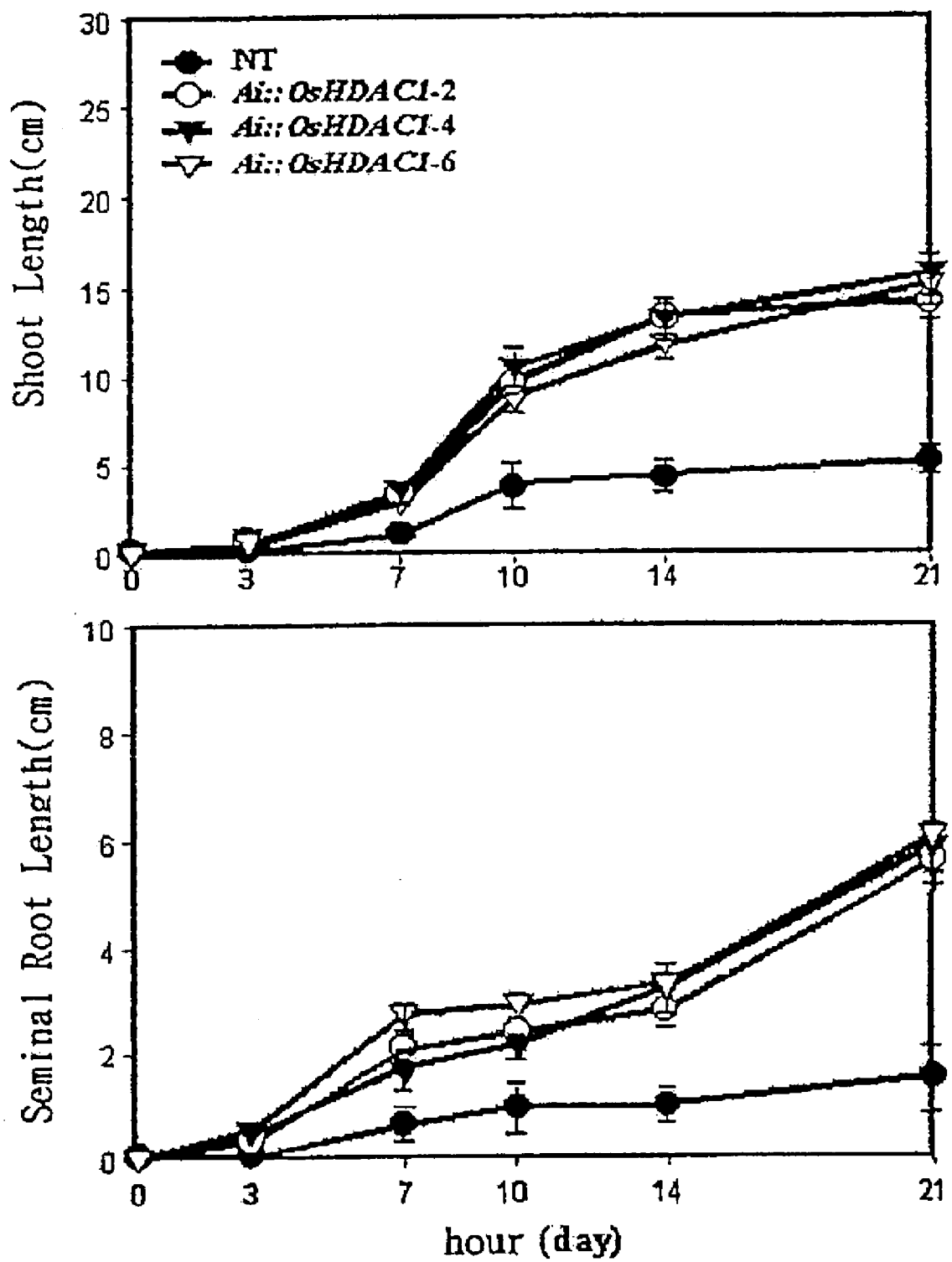

US 7,060,873 B2

METHOD FOR PRODUCING A PLANT WITH A HIGH-GROWTH RATE

BACKGROUND OF THE INVENTION

1. Field of the Invention

The present invention relates to a method for producing a plant having a high growth rate. More specifically, the present invention relates to proteins, OsHDAC1, OsHDAC2 and OsHDAC3, which function as a histone deacetylase, a gene coding for said proteins, and a method for producing a plant having a high growth rate by expressing said gene in the plant.

2. Description of the Related Art

Acetylation and deacetylation of histone are basic mechanisms to control the transcription of eukaryotic organisms wherein histone acetyltransferases (HATs) loose nucleosome by acetylation of histone to stimulate transcription, and histone deacetylases (HDACs) play a role of inhibiting the transcription through inhibition of the activity of HATs. The HDACs found in mammals can be classified generally into two classes: the HDACs belonging to class I, composed of approximately 400 to 500 amino acids having a homology with RPD3 as histone deacetylase of yeast, and the HDACs belonging to class II, composed of approximately 1000 amino acids having a homology with yeast's HDA1. Up to the present, HDACs have been very extensively studied and are known only in mammals and yeast, whereas plant HDACs have been known only in that they may be related to the failure of phenotypic function in the Arabidopsis and maize plant.

ABA (abscisic acid) is a plant hormone related to various physiological reactions including those against environmental stresses such as seed generation, dormancy or drought, high concentration of salts and cold. It has been known that abscisic acid plays an important role in maintaining the survival of the plant body by inhibiting the germination and growth of seeds and buds when the plant is under unsuitable growth conditions (see, Seo, M. and Koshiba, T., Trends Plant Sci., 7: 41–48, 2002). However, in monocot plants including rice, barley, wheat and maize for food production, it is more important that the productivity be increased by maintaining growth under unsuitable environmental conditions, than the maintenance of survival.

Therefore, there is a continuous need for developing the plant body, which can be maintained at a high growth rate even under stress conditions.

Thus, the present inventors have earnestly and extensively studied to develop a plant body having a high growth rate even under stress conditions. As a result, we have identified that OsHDAC1, among the three kinds of OsHDAC genes isolated from the rice plant, is expressed locally in the whole plant body, and when it is overexpressed, it changes the growth rate and phenotype of the plant and increases the growth of the plant body through increasing its expression even in the presence of ASA which inhibits germination and growth, and thus, completed the present invention.

Ultimately, the main purpose of the present invention is to provide protein OsHDACs that function as a histone deacetylase.

Another purpose of the present invention is to provide a gene OsHDAC coding for said protein.

Further, another purpose of the present invention is to provide a method for producing a plant body having a high growth rate which comprises the step of expressing said OsHDAC genes in the plant body.

SUMMARY OF THE INVENTION

The present invention relates to a protein, OsHDAC1, represented by an amino acid sequence of SEQ. ID. NO. 13 that functions as a histone deacetylase, a gene coding for OsHDAC1 as defined in SEQ. ID. NO. 13, and an OsHDAC1 gene coding for OsHDAC1 as defined in SEQ. ID. NO. 13 and represented by an amino acid sequence of SEQ. ID. NO.1. The present invention also relates to a protein, OsHDAC2, represented by an amino acid sequence of SEQ. ID. NO. 14 that functions as a histone deacetylase, a gene coding for OsHDAC2 as defined in SEQ. ID. NO. 14, and an OsHDAC2 gene coding for OsHDAC2 as defined in SEQ. ID. NO. 14 and represented by an amino acid sequence of SEQ. ID. NO.2. The present invention further relates to a protein, OsHDAC3, represented by an amino acid sequence of SEQ. ID. NO. 15 that functions as a histone deacetylase, a gene coding for OsHDAC3 as defined in SEQ. ID. NO. 15, and an OsHDAC3 gene coding for OsHDAC3 as defined in SEQ. ID. NO. 15 and represented by an amino acid sequence of SEQ. ID. NO. 3.

In addition, the present invention further relates to a method for producing a plant having a high growth rate, which comprises the step of transforming a monocot plant with a recombinant plasmid containing a gene coding for OsHDAC1, a gene coding for OsHDAC2, or a gene coding for OsHDAC3 to express the protein OsHDAC1, OsHDAC2 or OsHDAC3, respectively. Preferably, the high growth rate monocot plant produced by method of the present invention is rice, barley, wheat or maize. The method for producing a plant having a high growth rate according the present invention, can be further characterized in that the expression of OsHDAC1, OsHDAC2 or OsHDAC3 protein is increased by ASA (abscisic acid). The method for producing plant having a high growth rate according to the present invention is also characterized in that the plant exhibits a change in phenotypic properties. In addition the method for producing a plant having a high growth rate according to the present invention comprises the step of transforming a monocot plant with a recombinant plasmid containing a gene as defined in SEQ ID. NO. 1, SEQ. ID. NO. 2 or SEQ. ID. NO. 3, to express a protein OsHDAC1, OsHDAC2 or OsHDAC3, respectively.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying figures in which:

FIG. 1 is a drawing which shows the hybridizing position of probes 1, 2, 3, 4 and 5 in OsHDAC1, OsHDAC2 and OsHDAC3 cDNAs;

FIG. 2 is a drawing, which shows the genetic structures of OsHDAC1, OsHDAC2 and OsHDAC3;

FIG. 3 is a genetic map showing plasmid pAi-OsHDAC1;

FIG. 4 is a photograph showing the result of Northern blot analysis, which demonstrates the level of transcription of leaves, roots and callus cells of ABA-treated Ai::OsHDAC1 rice plant;

FIG. 5 is a photograph showing the result of Northern blot analysis, which demonstrates the effect of TSA on the reduction of acetylated H4 in callus cells of Ai::OsHDAC1 rice plant;

FIGS. 6a, 6b, 6c and 6d are photographs showing the growth and morphological change of Ai::OsHDAC1 rice plant, the change in the growth of leaves, the change of collars, and the change of roots, respectively; and FIGS. 7a and 7b are the graphs showing the growth of buds and deferential roots of Ai::OsHDAC1 rice plant in the absence and presence of ABA, respectively.

DETAILED DESCRIPTION OF THE INVENTION

The present inventors have paid attention to genes or proteins, which control the transcription of genes, particularly HDACs inhibiting the transcription of genes, as the target for changing the growth of plants. Thus, in order to separate plant HDACs genes we have searched the database for expressed sequence tags of rice plant to isolate three kinds of related genes, which are then designated as 'OsHDAC1', 'OsHDAC2' and 'OsHDAC3', respectively. The EST database contains, randomly, the partial base sequences of genes and genomes but does not have any information on the kinds and functions of genes. Therefore, in order to confirm whether the isolated gene actually plays a role or functions as a HDACs, first, a probe was constructed from an isolated gene and then the related genes were separated from a library of rice genes using said probe and amplified. Then, their base sequences and protein sequences were determined to analyze their structures, and thus it could be identified that respective genes contain the structures and sequences conserved in HDACs of mammals. Further, by carrying out Southern blot and Northern blot analysis using rice genomes and RNAs it has been identified that said three kinds of genes belong to the same category, are present with a single copy number in the genome, and are tissue-specifically expressed only except for OsHDAC1. From immunoblot analysis using histone protein purified from callus of rice plant transformed with OsHDAC1 and anti-tetraacetylated histone H4 antibody, it could also be identified that OsHDAC1 protein expressed from said OsHDAC1 gene acts as the normal HDAC. In view of the above findings, it was demonstrated that OsHDAC1, OsHDAC1 and OsHDAC1 genes isolated from EST database are HDACs gene of rice plant. Said three genes have been registered as GenBank accession numbers AF 513382, AF513383 and AF513384, respectively.

Then, the present inventors have also observed the growth and phenotypic morphological change of Ai::OsHDAC1 rice, which is a rice plant transformed with said OsHDAC1. In view of the growth of the rice plant, it was identified that the OsHDAC1 gene introduced into the transformed Ai::OsHDAC1 rice plant is transcribed at a rate higher than the non-transformed rice plant even under normal conditions, and also is transcribed under the conditions treated with ABA as the growth-inhibiting hormone induced by stresses at a level higher than or comparable to those under normal conditions. For the phenotype, the growth of the leaves, collars and roots, the buds of the seeds and the deferential roots in the Ai::OsHDAC1 rice and the non-transformed rice plants were observed. It could be seen that the leaves and the collars of the Ai::OsHDAC1 rice plant are much more healthy and strong and provide a higher growth rate, in comparison to those of non-transformed rice plant. From the above results, it could be identified that the plant body having a high growth rate can be developed using the OsHDAC1 gene.

The method for producing the plant body having a high growth rate according to the present invention comprises the step of transforming the monocot plant with a recombinant plasmid containing the OsHDACs gene to express the OsHDACs proteins: For this purpose, the OsHDACs gene is the OsHDAC1, OsHDAC2 or OsHDAC3 gene, and the expression amount of the OsHDACs protein expressed from said gene can be increased by ASA (abscisic acid) as one of the plant hormones, which inhibits germination and growth, to increase the growth rate of the plant body and further to change the phenotypic characteristics. The monocot plants to be transformed according to the present invention can include rice, barley, wheat and maize, etc. According to the present invention, the OsHDACs proteins change the structure of chromatin to cause an increase or decrease in the expression of the foreign genes in the genomes, so that the plant body of which the phenotypic characteristics are changed can be produced by controlling the expression amount of the OsHDACs proteins. Particularly, since the OsHDAC1 gene is expressed locally in the plant and increases the growth rate of the plant by its overexpression and its expression is increased by ABA, this gene can be very efficiently used for producing plants having a high growth rate even under stress conditions including drought, cold, etc., as well as under normal conditions.

Hereinafter, the present invention will be more specifically illustrated through the following examples. It will be apparent to a person having an ordinary knowledge in the relevant technical field that these examples are intended only to specifically explain the present invention but are not construed to limit the scope of the present invention.

EXAMPLE 1

Isolation of Genes and Construction of Probes

In order to isolate the HDACs gene of a rice plant, the sequences in the GenBank database were searched to isolate a few cDNA fragments of about 300 to 400 bp. Then, clones containing said respective cDNA fragments were screened from clones of the EST database of rice and DNAs contained in clones were sequenced by means of base sequence analyzer (Applied Biosystems, USA) to determine finally three kinds of the whole cDNA gene sequences. The sequenced genes were designated as 'OsHDAC1 (SEQ. ID. NO. 1)', 'OsHDAC2 (SEQ. ID. NO. 2)' and 'OsHDAC3 (SEQ. ID. NO. 3)', respectively. Then, the probes for searching respective genes in the genome library of the rice plant were constructed. Each of said genetic cDNAs was inserted into SalI-NotI site of pBluescript SKII (Stratagene, USA) to obtain the recombinant plasmid. Then, the recombinant plasmid containing OsHDAC1 cDNA was cleaved with NcoI/BamHI, XhoI/NotI and PstI/NotI to obtain DNA fragments of 392 bp (probe 1, SEQ. ID. NO. 4), 1283 bp (probe 2, SEQ. ID. NO. 5), and 415 bp (probe 3, SEQ. ID. NO. 6), as the probes for OsHDAC1. The probes for OsHDAC2 and OsHDAC3 were obtained using the following primers:

(1) Primers for OsHDAC2 probes

```
Primer P1:
5'-ACGACCCTGACTCTGATATG-3';    (SEQ. ID. NO. 7)

and

Primer R1:
5'-CCATGGTGTTGGATAATTCT-3'     (SEQ. ID. NO. 8)
```

(2) Primers for OsHDAC3 probes

```
Primer P2:
5'-CAGCAGCTATGCACCAGAAG-3';    (SEQ. ID. NO. 9)

and

Primer R2:
5'-GCCTCCACGTCCAGTATTGC-3'     (SEQ. ID. NO. 10)
```

As the probes for OsHDAC2 and OsHDAC3, the product produced from reverse transcription by means of RT-PCR system (Promega, USA) using plasmids containing said primers and OsHDAC2 or OsHDAC3 was again amplified with PCR to obtain 292 bp (probe 4, SEQ. ID. NO. 11) and 249 bp (probe 5, SEQ. ID. NO. 12) DNA fragments, which were respectively separated with electrophoresis and then labeled with [α-$^{32}$P] together with said probe 1, probe 2 and probe 3 for OsHDAC1. FIG. 1 is the drawing which shows the hybridizing position of probes 1, 2, 3, 4 and 5 in OsHDAC1, OsHDAC2 and OsHDAC3 cDNAs wherein Nc, B, Xh, P, N, S and E denote NcoI, BamHI, XhoI, PstI, NotI, SalI and EcoRI sites, respectively.

Meanwhile, by means of the BLAST and NDASTAR programs, the protein sequences of the three kinds of said three cDNA genes were determined. As a result of the sequencing of the respective proteins OsHDAC1 (SEQ. ID. NO. 13), OsHDAC2 (SEQ. ID. NO. 14) and OsHDAC3 (SEQ. ID. NO. 15), it could be identified that the proteins are composed respectively of 518, 498 and 510 amino acids and have the molecular weights of 57.5, 55,9 and 56.5 kDa, and preserve 9 domains conserved in mammal HDAC and histidine residue. Thus, it was determined that the separated genes are HDACs gene belonging to class I. According to this, said three cDNA genes OsHDAC1, OsHDAC2 and OsHDAC3 were registered as rice histone deacetylase genes under GenBank accession numbers AF513382, AF513383 and AF513384, respectively.

EXAMPLE 2

Separation of OsHDAC1 Genomic DNA

The three cDNAs separated above were screened from genome library and amplified: Genome database (Beijing Genome Center) of rice plant (*Oryza sativa* L. ssp. Indica) was screened using OsHDAC1 cDNA separated above to discover a contiguous sequence 31135 consistent with 5'-terminal and 3528-bp of OsHDAC1. To determine the remaining portion of OsHDAC1 genomic DNA, the following primers P3 and R3 were determined from 3-UTR sequence of OsHDAC1 cDNA using PRIMER DESIGNER 4 program:

```
Primer P3:
5'-GGTGGTGTCTGAATCTCCTA-3';    (SEQ. ID. NO. 16)

and

Primer R3:
5'-AGATGGCATCAGTTACTAAG-3'.    (SEQ. ID. NO. 17)
```

PCR was conducted using said two primers and genomic DNA of rice plant (*Oryza saliva* cv. Nipponbare) to amplify genomic DNA of 5.9 kb, and then the amplified DNA was inserted into pGEM-T-Easy vector (Promega, USA) and analyzed for its base sequence.

In the same manner, OsHDAC2 and OsHDAC3 cDNAs and said primers P1 and R1 and P2 and R2 were used to obtain the relevant genomic DNA of which the base sequence was analyzed. Then, the sequences of cDNA and genomic DNA were compared with each other to classify exons and introns of OsHDACs gene. FIG. 2 is a drawing, which shows the genetic structures of OsHDAC1, OsHDAC2 and OsHDAC3 wherein the black box represents exons. As can be seen from FIG. 2, it could be identified that OsHDAC1 and OsHDAC3 contain 7 exons and 6 introns and OsHDAC2 contains 6 exons and 5 introns.

EXAMPLE 3

Isolation and Southern Blot Analysis of Genomic DNA

In order to investigate how many copy numbers of respective OsHDACs genes are present in nice genomes, the genomic DNA was extracted from leaves of rice plant (*Oryza sativa* ca. Nipponbare) grown in greenhouse by means of guanidine-surfactant lysis method using DNA-zolES (Molecular Research Center, USA). 5 µg of genomic DNA was cleaved with 5 kinds of restriction enzymes including HindIII, EcoRI, XbaI, BamHI and XhoI, and then subjected to electrophoresis on 1.0% (w/v) agarose gel, transferred to hybond N+ nylon membrane (Amersham Pharmacia, USA) and hybridized respectively with probes 1, 2, 3, 4 and 5. After hybridization, the membrane was washed, allowed to stand on the intensifying plate for a while and then analyzed with phospho-image analyzer (FLA 3000, Fuji, Japan).

As the result of analysis, it could be identified that OsHDAC2 and OsHDAC3 are the members consisting OsHDAC1 group and OsHDAC1, OsHDAC2 and OsHDAC3 are present at a single copy number in rice genome.

EXAMPLE 4

Isolation and Northern Blot Analysis of RNA

In order to investigate the expression patterns of OsHDAC1, OsHDAC2 and OsHDAC3 in various lice tissues, a total RNA was isolated from callus cells, roots and leaves of rice plant using guanidium/LiCl method. 10 µg of total RNA was denatured in 50% formamide, 2.2 M formaldehyde, 20 mM MOPS [3-(N-morpholino)-propanesulfonic acid] and 0.5 mM EDTA at 70° C. for 5 minutes, subjected to electrophoresis on 1% formaldehyde-agarose gel, transferred to hybond N+ nylon membrane, hybridized respectively with probes 1, 2, 3, 4 and 5, and then analyzed with the same method as in said Southern blot analysis. As the result of analysis, it was identified that the transcription product of OsHDAC1 is expressed in all of leaf, root and callus cells whereas the transcription products of OsHDAC2 and OsHDAC3 are not expressed in leaf tissues. Therefore, it could be seen that OsHDAC2 and OsHDAC3 are expressed specifically in roots and calluses.

EXAMPLE 5

Construction of Vector and Production of Transduced Rice Plant 0.4 kb Ai promoter, as ABA-inducible promoter, composed of ABA (abscisic acid)-reaction complex (ABRC3) from 1.8 kb OsHDAC1 cDNA and barley HVA22 gene (see, Shen, Q. and Ho, T. H., Plant Cell, 7: 295–307, 1995), CAMV 35S minimal promoter containing only −46 to +100 portion, and 5'-UTR from adhI gene of Arabidopsis was inserted into ClaI-NcoI and NcoI-NcoI sites of pSK-RTG promoter (see, Jang, I-C. et al., Mol. Breeding, 5: 453–461, 1999). Next, said plasmid was cleaved with ClaI and NotI to obtain 2.2 kb DNA fragment composed of Ai promoter and OsHDAC1 cDNA, which was then inserted into pSBG-M cleaved with ClaI/NotI to construct plasmid pAi-OsHDAC1 (see, FIG. 3). Rice plant was transformed with the resulting plasmid using Agrobacterium-mediated transformation and then grown in greenhouse. All of 25 rice plants were produced, and most of them were identified as having a proliferative property and a resistance against 0.5% Vasta solution. FIG. 3 is a genetic map showing plasmid pAi-OsHDAC1, wherein Ai-P is ABA-inducible promoter; 3'pinII is 3'-portion of potato protease inhibitor II gene; 35S is 35S promoter; bar is bar gene to exhibit a herbicide resistance; 3' nos is 3'-portion of nopaline synthase gene; and E, P and N denote EcoRI, PstI and NotI sites, respectively.

Southern and Northern blot analysis of the genomes of Ai::OsHDAC1 rice as transduced rice plant was carried out in the same maimer as above, except that OsHDAC1-specific probe 3 and 586 bp MAR probe b (SEQ. ID. NO. 18) prepared from HindIII DNA fragment of pUC-B1-X1 were used (see, Miynarova, L. et al., Plant Cell, 6:417–426, 1994). As the result of Southern blot and Northern blot analysis, it was identified that OsHDAC1 gene is present at 1 to 3 copy numbers in genomic DNA of Ai::OsHDAC1 rice plant and is expressed in all of rice tissues. The subsequent analysis was carried out with selecting the plant having a single copy number of OsHDAC1.

EXAMPLE 6

Effect of ABA Treatment

While leaves of Ai::OsHDAC1 rice plant produced by above Example 5 was incubated in MS medium with or without 20 μM ABA, a total RNA was isolated from leaves at regular intervals to examine the expression level of OsHDAC1 transcription product. As the result, it was identified that the expression of the transcription product reaches at the maximum level one hour after ABA treatment and rapidly decreases after 6 hours. Then, callus cells, leaves and roots of rice plant were incubated in MS medium with or without 20 μM ABA for one hour, and a total RNA was extracted. FIG. 4 is a photograph showing the result of Northern blot analysis, which demonstrates the level of transcription of leaves, roots and callus cells of ABA-treated Ai::OsHDAC1 rice plant, wherein NT is untransformed rice plant, and lanes 2, 4 and 6 represent respective individuals of Ai::OsHDAC1 rice plant incubated in MS medium with (+) or without (−) 20 μM ABA for one hour. As can be seen from FIG. 4, it could be identified that in case of ABA treatment, the expression level of OsHDAC1 transcription product in Ai::OsHDAC1 rice plant is 2 to 5 times in leaves, 2 to 6 times in roots, and 9 to 15 times in callus cells, as high as that in untransformed rice plant. Further, the same result could be confirmed from Western blot analysis of OsHDAC1 protein.

Meanwhile, in callus cells of Ai::OsHDAC1 rice plant two kinds of OsHDAC1 mRNA similar to those present in callus of untransformed normal rice plant were found. However, in normal callus cells short transcription products were expressed predominantly over long transcription products whereas in callus of Ai::OsHDAC1 rice plant long transcription products were predominant.

EXAMPLE 7

Analysis of Histone Acetylation

In order to investigate acetylation of histone, histone was purified from callus (see, Waterborg, J. H. et al., Arch. Biochem. Biophys. 256:167–178, 1987), mixed with the same amount of staining solution (7.4 M urea, 1.4 M $NH_3$ and 10 mM DTT), and then incubated for 5 hours. The culture was subjected to electrophoresis on acid/urea/Triton (AUT; 1 M acetic acid, 0.5% Triton X-100, 45 mM $NH_3$ and 16% acrylamide) comprising the upper layer gel prepared from 1 M acetic acid, 6.3 M urea and 4.4% acrylamide, in a buffer solution containing 0.2 M glycine and 1 M acetic acid. Next, the immunoblot analysis was conducted using anti-tetra-acetylated histone H4 antibody. As the result, it could be identified that the expression of tetra-acetylated histone H4 is greatly reduced in Ai::OsHDAC1 rice plant, and thus, OsHDAC1 protein expressed from introduced OsHDAC1 gene functions as the normal enzyme.

EXAMPLE 8

Effect of Tricostatin A (TSA) Treatment

Rice callus cells, leaves and roots were incubated in MS medium with (+) or without (−) 20 μM ABA for one hour, transferred to MS medium containing 20 μM ABA and 1 μM TSA, incubated for 1 to 6 hours and then subjected to TSA treatment. Next, about 0.1 g of rice tissues was pulverized, homogenized with a buffer solution containing 50 mM Tris-HCl (pH 8.0), 150 mM NaCl, 10% glycerol, 0.5% Triton X-100, 2 mM phenylmethanesulfonyl fluoride, 1 μg/ml aprotinine, 1 μg/ml pepstatin and 1 μg/ml leupeptin, and then incubated at 4° C. for one hour. After incubation, the mixed solution was centrifuged at 4° C. for 5 minutes, and the protein concentration was determined using Bradford solution (BioRad, USA). The protein extract was separated from 12% SDS gel, transferred to polyvinylidene difluoride (PVDF) membrane (Immobilon-P, Millipore), and then reacted with mouse HDAC1 (mHDAC1), histone H4 (H4), acetylated histone (AcH4), the secondary antibody wherein primary antibody to acetylated histone H4 (AcH4) (Upstate Biotechnology, USA) is combined with alkaline phosphatase. FIG. 5 is a photograph showing the result of Northern blot analysis, which demonstrates the effect of TSA on the reduction of acetylated H4 in callus cells of Ai::OsHDAC1 rice plant in which NT is callus cells of untransformed rice plant, AcH4 is acetylated histone H4, H4 is total histone H4, and PC is a core histone separated from chicken red cells Upstate Biotechnology, USA). As can be seen from FIG. 5, it could be identified that the expression level of tetra-acetylated histone H4 is greatly increased in both of Ai::OsHDAC1 rice plant and untransformed rice plant after TSA treatment but total H4 is substantially not changed. Thus, it was confirmed that the expression of tetra-acetylated histone H4 as reduced in Ai::OsHDAC1 rice plant is increased again by TSA treatment. This means that TSA specifically inhibits histone deacetylase to greatly increase the acetylation of histone.

EXAMPLE 9

Analysis of Phenotypic Characteristics

In order to investigate the effect of overexpression of OsHDAC1 on the phenotype and growth of Ai::OsHDAC1 rice plant, Ai::OsHDAC1 rice plant was incubated as the first generation and then, young seedlings or calluses at the second generation were transferred to MS medium with or without 20 μM ABA and incubated for 2 weeks. After incubation, the whole shape of rice plant, and leaves, collars and roots were observed. As the control group, untransformed rice plant was also observed. FIGS. 6a, 6b, 6c and 6d are photographs showing the growth and morphological change of Ai::OsHDAC1 rice plant, the change in the growth of leaves, the change of collars and the change of roots, respectively. In each drawing, NT denotes untransformed rice plant and lanes 2, 3 and 4 in FIGS. 6b, 6c and 6d denote respective individuals of transformed Ai::OsHDAC1 rice plant. As can be seen from FIG. 6a, untransformed plant exhibited the inhibition of growth in the presence of ABA and was killed after 2 to 3 weeks, whereas Ai::OsHDAC1 rice plant exhibits an increase of growth in the presence of ABA. Further, as can be seen from FIGS. 6b, 6c and 6d, leaves, collars and roots of Ai::OsHDAC1 were very healthy and strong in comparison to those of untransformed lice plant.

Further, buds and deferential roots of T2 seeds were also observed. FIGS. 7a and 7b are the graphs comparatively showing the growths of buds and deferential roots of Ai::OsHDAC1 rice plant and untransformed rice plant in the absence and presence of 20 μM ABA, respectively. As can be seen from FIGS. 7a and 7b, when the plant was incubated in MS medium containing 20 μM ABA, the seeds of Ai::OsHDAC1 rice plant exhibited a very rapid rate of bud germination and deferential root growth in comparison to that of the seeds of untransformed rice. The rice plant transformed with the control vector not containing OsHDAC1 gene did not show the characteristics shown in Ai::OsHDAC1 rice plant.

As specifically explained and demonstrated above, the present invention relates to a protein having a function of histone deacetylase, i.e. OsHDAC1, OsHDAC2 and OsHDAC3, a gene coding for said proteins, and a method for producing a plant having a high growth rate by expressing said gene in the plant. According to the present invention, OsHDACs proteins change the structure of chromatin to increase or decrease the expression of a foreign gene in genomes, so that the expression amount of OsHDACs proteins can be controlled to produce the plant having varied phenotypic characteristics. Particularly, OsHDAC1 gene is expressed locally in the plant and increases the growth rate of plant by its overexpression and its expression is increased by ABA. Therefore, it can be very efficiently used for producing plants having a high growth rate even under stress conditions including drought, cold, etc., as well as under the normal conditions.

What is claimed is:

1. An isolated nucleic acid sequence comprising SEQ ID NO: 1 and coding for OsHDAC1 protein.

2. The sequence of claim 1, encoding a protein having a function of histone deacetylase.

3. A method for producing a plant having an increased growth rate, which comprises the step of transforming a monocot plant with a recombinant plasmid containing an isolated nucleic acid sequence comprising SEQ ID NO: 1 to express a protein OsHDAC1.

4. The method for producing a plant having an increased growth rate according to claim 3, characterized in that the monocot plant is rice, barley, wheat or maize.

5. The method for producing a plant having an increased growth rate according to claim 3, characterized in that the expression of OsHDAC1 protein is increased by ABA (abscisic acid).

6. The method for producing a plant having an increased growth rate according to claim 3, characterized in that the plant exhibits a change in phenotypic properties.

7. A method for producing a plant having an increased growth rate, which comprises the step of transforming a monocot plant with a recombinant plasmid containing an isolated nucleic acid sequence comprising SEQ ID NO:1 and encoding a protein having a function of histone deacetylase to express a protein OsHDAC1.

* * * * *

SEQUENCE LISTING

<160> NUMBER OF SEQ ID NOS: 18

<210> SEQ ID NO 1
<211> LENGTH: 1859
<212> TYPE: DNA
<213> ORGANISM: Oryza sativa

<400> SEQUENCE: 1

```
ggggaaaaga aaaaaaaag agataaaaaa aaatctcct cctcctcgcc gccgccgccg        60
ccgccgccat ggacgcctcc gccggaggcg gggggaactc gctgccgacg gcggggggccg      120 acggggccaa gcggcgggtg tgctacttct acgacgcgga ggtggggaac tactactacg      180 ggcagggggca cccgatgaag ccgcaccgca tccggatgac ccacgcgctg ctcgcccact      240
acggcctcct cgaccagatg caggtgctca agccccaccc ggcgcgcgac cgcgacctct      300
gccgcttcca cgccgacgac tacgtcgcct tcctccgctc cgtcacgccg gagacccagc      360
aggaccagat ccgggcgctc aagcgcttca cgtcggcga ggactgcccc gtcttcgacg      420
gcctctacag cttctgccag acctacgccg ggggatccgt cggcggcgcc gtcaagctca      480
accacggcca cgacatcgcc atcaactggg ccggcggcct ccaccacgcc aagaagtgcg      540
aggcctcggg attctgctac gtcaacgaca tcgtcctcgc catcctcgag ctcctcaaat      600
accaccagcg tgttctctat gtggatatcg atatccacca tgggggatggt gtggaggagg      660
```

-continued

```
cgttctacac gacggacagg gtgatgacgg tctcgttcca caagtttggg gattatttcc      720
cggggaccgg ggacattcgc gatattgggc actcaaaggg gaagtattac tctctgaatg      780
tcccgttgga cgacggtatc gacgacgaga gctaccagtc gttgttcaag ccgatcatgg      840
ggaaggtgat ggaggttttt cgccctggcg cggtggtgct ccagtgcggt gcggactctc      900
tgtcgggtga taggttgggt tgcttcaacc tgtcaatcag gggccacgcg gaatgcgtga      960
gattcatgag gtccttcaat gtcccgctgt tgctgcttgg tggtggtggg tataccataa     1020
gaaatgttgc gcggtgttgg tgctatgaga caggagttgc acttggtcat gagctcactg     1080
acaagatgcc tccaaatgag tattttgagt actttggtcc agattataca cttcatgttg     1140
caccaagtaa catggagaac aaaaacacac gccagcagtt ggatgatata agatcaagac     1200
ttcttgataa tctttcaaaa cttcgacatg ctcctagcgt ccaatttcaa gagcgacccc     1260
ctgaggctga gctacctgag caagatgaag accaagagga tcctgatgaa aggcaccatg     1320
ctgattctga tgtggaaatg gatgatgtca aaccttggga tgactcagga aggaggagca     1380
gtattcagaa tgtgagagtt aagagagagt ctgctgaaac agatgccgca gatcaggatg     1440
gtaatagggt cgctgcagag aacaccaagg gcacagaacc tgcggctgat ggagttggtt     1500
cctcgaaaca aactgttcct accgatgcaa gtgcgatggc catagacgaa ccaggctccc     1560
tgaaagtcga gccagataac tcaaacaaat gcaagatca accatcggtg caccagaaga     1620
cataatagtt ctctctacct taaaacttag taactgatgc catctatcat ccattgatta     1680
tattggagaa actcccaact ttgaagcaga gagttcatgc cataccaaaa gttatatacc     1740
aaatttcgaa tggtatgtac accttcgaa ctggtggtgt tttgtgcaat acatttatgc     1800
caggctgact attatgtggt atctattatt agctttagtt taaaaaaaaa aaaaaaaaa     1859
```

<210> SEQ ID NO 2
<211> LENGTH: 1703
<212> TYPE: DNA
<213> ORGANISM: Oryza sativa

<400> SEQUENCE: 2

```
atcgctcgcc tcctctgctt cgcttccttc tccagcaagc acccgaccac aacacacacg       60
cgagctcctc gacctcgaga gagagagaaa acccaacccc gaattcggcg gcggaggcgg      120
aggcagcggc gatggacccc tcgtcggcgg gcgccggcgg caactcgctg gcgtcggcgt      180
cgtgcggcga cgcgcagaag cggcgggtgt gctacttcta cgatccggag gtgggcaact      240
actactacgg gcagggtcac ccgatgaagc cccaccgcgt gaggatgacc cacgcgctgc      300
tcgcccacta cggcctcctc gccccggcca agatgcaggt gctccgcccg ctccccgccc      360
gcgaccgcga cctctgccgc ttccactccg acgactacgc cgccttcctc cgcgccgtca      420
ccccggagac ccagttcgac cagatccgct ccctccgccg cttcaacgtc ggcgaggact      480
gccccgtctt cgacggcctc tacgcctact gccagaccta cgcgggggcc tcgtcggcg      540
ccgccgtcaa gctcaaccac ggcacccacg acatcgccat caactggtcc ggcgggttgc      600
accacgccaa gaagtccgag gcctccggct ctgctacgt caacgacatc gtcctcgcca      660
tcctcgagct cctcaagctc catgagcgag ttctgtatat tgatattgat atccatcatg      720
gagatggagt tgaggaggca ttctacacaa caaacagggt tatgacagtc tcatttcaca      780
agtttgggga ttatttcccg ggaacagggg acatccgcga tattgggtat tcagaaggga      840
agtattactg cctgaatgtc ccgctggatg atggaattga tgatgacagc taccagtcca      900
tcttcaagcc gatcatcagc aaagtcatgg agatgtatcg tcctggtgca gtcgtgcttc      960
```

```
agtgcggcgc tgattcgttg tccggtgata ggttgggctg tttcaatctc tcaggcaaag   1020
gtcatgctga atgtgttaag ttcatgaggt ctttcaatgt tccgttgctt cttcttggtg   1080
gtggtggata taccataaga aatgttgcac gctgctggtg ttacgagaca ggagttgcac   1140
ttggtgaaga gctacgggag aagttgcctt ataacgagta ttatgaatat tttggtccag   1200
aatacagtct ttacgttgca gcaagtaaca tggagaacag aaatacaaac aagcaattgg   1260
aggaaataaa atgcaacatt ctggacaatc tctcaaaact tcaacatgct cctagtgtcc   1320
aatttgaaga gcgaattcct gaaacaaagc tacctgagcc agatgaagat caagatgatc   1380
cagatgaaag gcacgaccct gactctgata tgctgttgga tgatcacaaa cctatgggac   1440
actcagcaag aagccttatt cacaacatcg gagttaagag agaaattact gaaacagaga   1500
ccaaagatca gcatggtaag agattaacaa ctgaacataa agtaccagaa ccgatggcag   1560
acgatcttgg ttcctccaag caagttcctg taagtcgtcg tcttctctat ccatctgcaa   1620
atccatagca caaactctgc attgcataat gcctatatgg atatagaatt atccaacacc   1680
atggtttaat ctgctctaac aaa                                           1703

<210> SEQ ID NO 3
<211> LENGTH: 2043
<212> TYPE: DNA
<213> ORGANISM: Oryza sativa

<400> SEQUENCE: 3
cagcaagcac ccgaccacaa cacacacgcg agcttctcga gagaggaaaa aaacccaacc     60
ccgaattcgg cggcggcggc ggaggcggag gcggcgatgg acccctcgtc ggcgggcgcg    120
ggcggcaact cgctggcgtc ggcgtcgtgc ggcgacgcgc agaagcggcg ggtgtgctac    180
ttctacgacc cggaggtggg caactactac tacggtcagg gccacccgat gaagccccac    240
cgggtgagga tgacccacgc gctgctcgcc cactacggcc tcctcgcccc ggccaagatg    300
gaggtgctcc gcccgctccc cgcccgcggc atcgacctct gccgcttcca ctccgacgac    360
tacgtcgcct tctcccgcgc cgtcaccccg gagacccagc tcggccaggt ccgcgccctc    420
cgccgcttca acatcggccc ggactgcccc gtcttcgacg gcctctacgc ctactgccag    480
acctacgcgg gggcctccgt cggcgccgcc gtcaagctca accacggcac ccacgacatc    540
gccatcaact ggtccggcgg gttgcaccac gccaagaagt ccgaggcctc cggcttctgc    600
tacgtcaacg catcgtcct cgccatcctc gagctcctca agctccatga gcgagttctg    660
tatattgata ttgatatcca tcatggagat ggagttgagg aggcattcta cacaacaaac    720 agggtttatga cagtctcatt tcacaagttt ggggattatt tcccgggaac aggggatatc    780
cgcgacattg gtattcaga agggaagtat tactgcctga atgtcccgct ggatgatgga    840
attgatgatg acagctacca gtccatcttc aagccgatca tcagcaaagt catggagatg    900
tatcgtcctg gtgcagtcgt gcttcagtgc ggcgctgatt cgttgtccgg tgataggttg    960
ggctgtttca atctctcagg gaaaggtcat gctgaatgtg ttaagttcat gaggtctttc   1020
aatgttccgt tgcttcttct tggtggtggt ggatatacca taagaaatgt tgcacgctgc   1080
tggtgttacg agacaggagt tgcacttggt gaagagctac aggagaagtt gccttacaat   1140
gagtattatg aatattttgg tccagaatac agtctttacg ttgcagcaag taacatggag   1200
aacagaaata caaacaagca actggaggaa ataaaatgca atattctgga caatctttca   1260
aaacttcaac atgcacctag cgtccaattt caagagcgaa ttcctgaaac aaagctacct   1320
```

| | |
|---|---:|
| gagccagatg aagatcaaga ggatccagat gaaaggcacg accctgactc tgatatggtg | 1380 |
| ttggatgatc acaaacctac gggacactca gcaagaagcc ttattcacaa catcggagta | 1440 |
| aagagagaaa ttactgaaac agagaccaaa gatcagcatg gtaagagatt aacaaccgaa | 1500 |
| cataaaggac cagaaccgat ggcagaggat cttggttcct ccaagcaagc tcctactgcg | 1560 |
| gatgcaaatg cggtggccgt caacgcgcca ggcaacgcca ggaatgaacc gggaagctca | 1620 |
| cccaaatgac cgaacccacc agcagctatg caccagaaga ccatgattta gctaccttca | 1680 |
| ggacacgagc tctctgtcaa ggtttcctgc atgctcttaa gttggcagaa actggagttg | 1740 |
| atctgtatac tgcatcttga catttcaaac ttaaaaatcg acacaaatca agagcaaaca | 1800 |
| ctgtttgatt gtttcttctg taggagttta ccattgtttc ttttgttgaa gaagtccata | 1860 |
| atgttcaggc aatactggac gtggaggcat tagtctgact gaccaatgta gtacaaaaca | 1920 |
| aaacatgtaa cgtgaagcaa gttaaaatgt acagtctgtt agactgttag atggagatat | 1980 |
| ggaatttcag gcgaaaaaaa aaaaaaaaa aaaaaaaaa aaaaaaaaa aaaaaaaaa | 2040 |
| aaa | 2043 |

<210> SEQ ID NO 4
<211> LENGTH: 392
<212> TYPE: DNA
<213> ORGANISM: Artificial Sequence
<220> FEATURE:
<223> OTHER INFORMATION: probe 1

<400> SEQUENCE: 4

| | |
|---|---:|
| ccatggacgc ctccgccgga ggcgggggga actcgctgcc gacggcgggg gccgacgggg | 60 |
| ccaagcggcg ggtgtgctac ttctacgacg cggaggtggg gaactactac tacgggcagg | 120 |
| ggcacccgat gaagccgcac cgcatccgga tgacccacgc gctgctcgcc cactacggcc | 180 |
| tcctcgacca gatgcaggtg ctcaagcccc accggcgcg cgaccgcgac ctctgccgct | 240 |
| tccacgccga cgactacgtc gccttcctcc gctccgtcac gccggagacc cagcaggacc | 300 |
| agatccgggc gctcaagcgc ttcaacgtcg cgcgaggactg ccccgtcttc gacggcctct | 360 |
| acagcttctg ccagacctac gccgggggat cc | 392 |

<210> SEQ ID NO 5
<211> LENGTH: 1283
<212> TYPE: DNA
<213> ORGANISM: Artificial Sequence
<220> FEATURE:
<223> OTHER INFORMATION: probe 2

<400> SEQUENCE: 5

| | |
|---|---:|
| ctcgagctcc tcaaatacca ccagcgtgtt ctctatgtgg atatcgatat ccaccatggg | 60 |
| gatggtgtgg aggaggcgtt ctacacgacg gacagggtga tgacggtctc gttccacaag | 120 |
| tttgggatt atttcccggg gaccggggac attcgcgata ttgggcactc aaaggggaag | 180 |
| tattactctc tgaatgtccc gttggacgac ggtatcgacg acgagagcta ccagtcgttg | 240 |
| ttcaagccga tcatggggaa ggtgatggag gttttcgcc ctggcgcggt ggtgctccag | 300 |
| tgcggtgcgg actctctgtc gggtgatagg ttgggttgct caacctgtc aatcagggc | 360 |
| cacgcggaat gcgtgagatt catgaggtcc ttcaatgtcc cgctgttgct gcttggtggt | 420 |
| ggtgggtata ccataagaaa tgttgcgcgg tgttggtgct atgagacagg agttgcactt | 480 |
| ggtcatgagc tcactgacaa gatgcctcca aatgagtatt tgagtacttt tggtccagat | 540 |
| tatacacttc atgttgcacc aagtaacatg gagaacaaaa acacacgcca gcagttggat | 600 |

```
gatataagat caagacttct tgataatctt tcaaaacttc gacatgctcc tagcgtccaa    660
tttcaagagc gaccccctga ggctgagcta cctgagcaag atgaagacca agaggatcct    720
gatgaaaggc accatgctga ttctgatgtg gaaatggatg atgtcaaacc tttggatgac    780
tcaggaagga ggagcagtat tcagaatgtg agagttaaga gagagtctgc tgaaacagat    840
gccgcagatc aggatggtaa tagggtcgct gcagagaaca ccaagggcac agaacctgcg    900
gctgatggag ttggttcctc gaaacaaact gttcctaccg atgcaagtgc gatggccata    960
gacgaaccag gctccctgaa agtcgagcca gataactcaa acaaattgca agatcaacca   1020
tcggtgcacc agaagacata atagttctct ctaccttaaa acttagtaac tgatgccatc   1080
tatcatccat tgattatatt ggagaaactc ccaactttga agcagagagt tcatgccata   1140
ccaaaagtta tataccaaat ttcgaatggt atgtacacct ttcgaactgg tggtgttttg   1200
tgcaatacat ttatgccagg ctgactatta tgtggtatct attattagct ttagtttaaa   1260
aaaaaaaaaa aaaaagcggc cgc                                          1283

<210> SEQ ID NO 6
<211> LENGTH: 415
<212> TYPE: DNA
<213> ORGANISM: Artificial Sequence
<220> FEATURE:
<223> OTHER INFORMATION: probe 3

<400> SEQUENCE: 6
ctgcagagaa caccaagggc acagaacctg cggctgatgg agttggttcc tcgaaacaaa     60
ctgttcctac cgatgcaagt gcgatggcca tagacgaacc aggctccctg aaagtcgagc    120
cagataactc aaacaaattg caagatcaac catcggtgca ccagaagaca taatagttct    180
ctctacctta aaacttagta actgatgcca tctatcatcc attgattata ttggagaaac    240
tcccaacttt gaagcagaga gttcatgcca taccaaaagt tataccaa atttcgaatg    300 gtatgtacac ctttcgaact ggtggtgttt tgtgcaatac atttatgcca ggctgactat    360
tatgtggtat ctattattag ctttagttta aaaaaaaaaa aaaaaagcg gccgc         415

<210> SEQ ID NO 7
<211> LENGTH: 20
<212> TYPE: DNA
<213> ORGANISM: Artificial Sequence
<220> FEATURE:
<223> OTHER INFORMATION: primer P1

<400> SEQUENCE: 7
acgaccctga ctctgatatg                                                20

<210> SEQ ID NO 8
<211> LENGTH: 20
<212> TYPE: DNA
<213> ORGANISM: Artificial Sequence
<220> FEATURE:
<223> OTHER INFORMATION: primer R1

<400> SEQUENCE: 8
ccatggtgtt ggataattct                                                20

<210> SEQ ID NO 9
<211> LENGTH: 20
<212> TYPE: DNA
<213> ORGANISM: Artificial Sequence
<220> FEATURE:
```

-continued

<223> OTHER INFORMATION: primer P2

<400> SEQUENCE: 9
cagcagctat gcaccagaag                                                    20

<210> SEQ ID NO 10
<211> LENGTH: 20
<212> TYPE: DNA
<213> ORGANISM: Artificial Sequence
<220> FEATURE:
<223> OTHER INFORMATION: primer R2

<400> SEQUENCE: 10
gcctccacgt ccagtattgc                                                    20

<210> SEQ ID NO 11
<211> LENGTH: 292
<212> TYPE: DNA
<213> ORGANISM: Artificial Sequence
<220> FEATURE:
<223> OTHER INFORMATION: probe 4

<400> SEQUENCE: 11
acgaccctga ctctgatatg ctgttggatg atcacaaacc tatgggacac tcagcaagaa        60
gccttattca acatcggag gttaagagag aaattactga acagagacc aaagatcagc         120 atggtaagag attaacaact gaacataaag taccagaacc gatggcagac gatcttggtt       180
cctccaagca agttcctgta agtcgtcgtc ttctctatcc atctgcaaat ccatagcaca       240
aactctgcat tgcataatgc ctatatggat atagaattat ccaacaccat gg               292

<210> SEQ ID NO 12
<211> LENGTH: 249
<212> TYPE: DNA
<213> ORGANISM: Artificial Sequence
<220> FEATURE:
<223> OTHER INFORMATION: probe 5

<400> SEQUENCE: 12
cagcagctat gcaccagaag accatgattt agctaccttc aggacacgag ctctctgtca       60
aggtttcctg catgctctta agttggcaga aactggagtt gatctgtata ctgcatcttg      120
acatttcaaa cttaaaaatc gacacaaatc aagagcaaac actgtttgat tgtttcttct     180
gtaggagttt accattgttt cttttgttga agaagtccat aatgttcagg caatactgga     240
cgtggaggc                                                              249

<210> SEQ ID NO 13
<211> LENGTH: 518
<212> TYPE: PRT
<213> ORGANISM: Oryza sativa

<400> SEQUENCE: 13

Met Asp Ala Ser Ala Gly Gly Gly Asn Ser Leu Pro Thr Ala Gly
  1               5                  10                  15

Ala Asp Gly Ala Lys Arg Arg Val Cys Tyr Phe Tyr Asp Ala Glu Val
                 20                  25                  30

Gly Asn Tyr Tyr Tyr Gly Gln Gly His Pro Met Lys Pro His Arg Ile
             35                  40                  45

Arg Met Thr His Ala Leu Leu Ala His Tyr Gly Leu Leu Asp Gln Met
         50                  55                  60

Gln Val Leu Lys Pro His Pro Ala Arg Asp Arg Asp Leu Cys Arg Phe

```
              65                  70                  75                  80
His Ala Asp Asp Tyr Val Ala Phe Leu Arg Ser Val Thr Pro Glu Thr
                    85                  90                  95
Gln Gln Asp Gln Ile Arg Ala Leu Lys Arg Phe Asn Val Gly Glu Asp
                100                 105                 110
Cys Pro Val Phe Asp Gly Leu Tyr Ser Phe Cys Gln Thr Tyr Ala Gly
                115                 120                 125
Gly Ser Val Gly Gly Ala Val Lys Leu Asn His Gly His Asp Ile Ala
        130                 135                 140
Ile Asn Trp Ala Gly Leu His His Ala Lys Lys Cys Glu Ala Ser
145                 150                 155                 160
Gly Phe Cys Tyr Val Asn Asp Ile Val Leu Ala Ile Leu Glu Leu Leu
                165                 170                 175
Lys Tyr His Gln Arg Val Leu Tyr Val Asp Ile Asp Ile His His Gly
                180                 185                 190
Asp Gly Val Glu Glu Ala Phe Tyr Thr Thr Asp Arg Val Met Thr Val
                195                 200                 205
Ser Phe His Lys Phe Gly Asp Tyr Phe Pro Gly Thr Gly Asp Ile Arg
        210                 215                 220
Asp Ile Gly His Ser Lys Gly Lys Tyr Tyr Ser Leu Asn Val Pro Leu
225                 230                 235                 240
Asp Asp Gly Ile Asp Asp Glu Ser Tyr Gln Ser Leu Phe Lys Pro Ile
                245                 250                 255
Met Gly Lys Val Met Glu Val Phe Arg Pro Gly Ala Val Val Leu Gln
                260                 265                 270
Cys Gly Ala Asp Ser Leu Ser Gly Asp Arg Leu Gly Cys Phe Asn Leu
                275                 280                 285
Ser Ile Arg Gly His Ala Glu Cys Val Arg Phe Met Arg Ser Phe Asn
        290                 295                 300
Val Pro Leu Leu Leu Gly Gly Gly Gly Tyr Thr Ile Arg Asn Val
305                 310                 315                 320
Ala Arg Cys Trp Cys Tyr Glu Thr Gly Val Ala Leu Gly His Glu Leu
                325                 330                 335
Thr Asp Lys Met Pro Pro Asn Glu Tyr Phe Glu Tyr Phe Gly Pro Asp
                340                 345                 350
Tyr Thr Leu His Val Ala Pro Ser Asn Met Glu Asn Lys Asn Thr Arg
        355                 360                 365
Gln Gln Leu Asp Asp Ile Arg Ser Arg Leu Leu Asp Asn Leu Ser Lys
        370                 375                 380
Leu Arg His Ala Pro Ser Val Gln Phe Gln Glu Arg Pro Pro Glu Ala
385                 390                 395                 400
Glu Leu Pro Glu Gln Asp Glu Asp Gln Glu Asp Pro Asp Glu Arg His
                405                 410                 415
His Ala Asp Ser Asp Val Glu Met Asp Val Lys Pro Leu Asp Asp
                420                 425                 430
Ser Gly Arg Arg Ser Ser Ile Gln Asn Val Arg Val Lys Arg Glu Ser
        435                 440                 445
Ala Glu Thr Asp Ala Ala Asp Gln Asp Gly Asn Arg Val Ala Ala Glu
        450                 455                 460
Asn Thr Lys Gly Thr Glu Pro Ala Ala Asp Gly Val Gly Ser Ser Lys
465                 470                 475                 480
Gln Thr Val Pro Thr Asp Ala Ser Ala Met Ala Ile Asp Glu Pro Gly
                485                 490                 495
```

```
Ser Leu Lys Val Glu Pro Asp Asn Ser Asn Lys Leu Gln Asp Gln Pro
            500                 505                 510
Ser Val His Gln Lys Thr
        515

<210> SEQ ID NO 14
<211> LENGTH: 498
<212> TYPE: PRT
<213> ORGANISM: Oryza sativa

<400> SEQUENCE: 14

Met Asp Pro Ser Ser Ala Gly Ala Gly Gly Asn Ser Leu Ala Ser Ala
  1               5                  10                  15

Ser Cys Gly Asp Ala Gln Lys Arg Arg Val Cys Tyr Phe Tyr Asp Pro
             20                  25                  30

Glu Val Gly Asn Tyr Tyr Tyr Gly Gln Gly His Pro Met Lys Pro His
         35                  40                  45

Arg Val Arg Met Thr His Ala Leu Leu Ala His Tyr Gly Leu Leu Ala
     50                  55                  60

Pro Ala Lys Met Gln Val Leu Arg Pro Leu Ala Arg Asp Arg Asp
 65                  70                  75                  80

Leu Cys Arg Phe His Ser Asp Asp Tyr Val Ala Phe Leu Arg Ala Val
                 85                  90                  95

Thr Pro Glu Thr Gln Phe Asp Gln Ile Arg Ser Leu Arg Arg Phe Asn
            100                 105                 110

Val Gly Glu Asp Cys Pro Val Phe Asp Gly Leu Tyr Ala Tyr Cys Gln
        115                 120                 125

Thr Tyr Ala Gly Ala Ser Val Gly Ala Ala Val Lys Leu Asn His Gly
    130                 135                 140

Thr His Asp Ile Ala Ile Asn Trp Ser Gly Gly Leu His His Ala Lys
145                 150                 155                 160

Lys Ser Glu Ala Ser Gly Phe Cys Tyr Val Asn Asp Ile Val Leu Ala
                165                 170                 175

Ile Leu Glu Leu Leu Lys Leu His Glu Arg Val Leu Tyr Ile Asp Ile
            180                 185                 190

Asp Ile His His Gly Asp Gly Val Glu Glu Ala Phe Tyr Thr Thr Asn
        195                 200                 205

Arg Val Met Thr Val Ser Phe His Lys Phe Gly Asp Tyr Phe Pro Gly
    210                 215                 220

Thr Gly Asp Ile Arg Asp Ile Gly Tyr Ser Glu Gly Lys Tyr Tyr Cys
225                 230                 235                 240

Leu Asn Val Pro Leu Asp Asp Gly Ile Asp Asp Ser Tyr Gln Ser
                245                 250                 255

Ile Phe Lys Pro Ile Ile Ser Lys Val Met Glu Met Tyr Arg Pro Gly
            260                 265                 270

Ala Val Val Leu Gln Cys Gly Ala Asp Ser Leu Ser Gly Asp Arg Leu
        275                 280                 285

Gly Cys Phe Asn Leu Ser Gly Lys Gly His Ala Glu Cys Val Lys Phe
    290                 295                 300

Met Arg Ser Phe Asn Val Pro Leu Leu Leu Gly Gly Gly Gly Tyr
305                 310                 315                 320

Thr Ile Arg Asn Val Ala Arg Cys Trp Cys Tyr Glu Thr Gly Val Ala
                325                 330                 335

Leu Gly Glu Glu Leu Arg Glu Lys Leu Pro Tyr Asn Glu Tyr Tyr Glu
```

-continued

```
                340                 345                 350
Tyr Phe Gly Pro Glu Tyr Ser Leu Tyr Val Ala Ala Ser Asn Met Glu
            355                 360                 365

Asn Arg Asn Thr Asn Lys Gln Leu Glu Glu Ile Lys Cys Asn Ile Leu
        370                 375                 380

Asp Asn Leu Ser Lys Leu Gln His Ala Pro Ser Val Gln Phe Glu Glu
385                 390                 395                 400

Arg Ile Pro Glu Thr Lys Leu Pro Glu Pro Asp Glu Asp Gln Asp Asp
                405                 410                 415

Pro Asp Glu Arg His Asp Pro Asp Ser Asp Met Leu Leu Asp Asp His
            420                 425                 430

Lys Pro Met Gly His Ser Ala Arg Ser Leu Ile His Asn Ile Gly Val
        435                 440                 445

Lys Arg Glu Ile Thr Glu Thr Glu Thr Lys Asp Gln His Gly Lys Arg
        450                 455                 460

Leu Thr Thr Glu His Lys Val Pro Glu Pro Met Ala Asp Asp Leu Gly
465                 470                 475                 480

Ser Ser Lys Gln Val Pro Val Ser Arg Arg Leu Leu Tyr Pro Ser Ala
                485                 490                 495

Asn Pro

<210> SEQ ID NO 15
<211> LENGTH: 510
<212> TYPE: PRT
<213> ORGANISM: Oryza sativa

<400> SEQUENCE: 15

Met Asp Pro Ser Ser Ala Gly Ala Gly Gly Asn Ser Leu Ala Ser Ala
  1               5                  10                  15

Ser Cys Gly Asp Ala Gln Lys Arg Arg Val Cys Tyr Phe Tyr Asp Pro
                 20                  25                  30

Glu Val Gly Asn Tyr Tyr Tyr Gly Gln Gly His Pro Met Lys Pro His
             35                  40                  45

Arg Val Arg Met Thr His Ala Leu Leu Ala His Tyr Gly Leu Leu Ala
         50                  55                  60

Pro Ala Lys Met Glu Val Leu Arg Pro Leu Pro Ala Arg Gly Ile Asp
 65                  70                  75                  80

Leu Cys Arg Phe His Ser Asp Asp Tyr Val Ala Phe Leu Arg Ala Val
                 85                  90                  95

Thr Pro Glu Thr Gln Leu Gly Gln Val Arg Ala Leu Arg Arg Phe Asn
            100                 105                 110

Ile Gly Pro Asp Cys Pro Val Phe Asp Gly Leu Tyr Ala Tyr Cys Gln
        115                 120                 125

Thr Tyr Ala Gly Ala Ser Val Gly Ala Ala Val Lys Leu Asn His Gly
130                 135                 140

Thr His Asp Ile Ala Ile Asn Trp Ser Gly Gly Leu His His Ala Lys
145                 150                 155                 160

Lys Ser Glu Ala Ser Gly Phe Cys Tyr Val Asn Asp Ile Val Leu Ala
                165                 170                 175

Ile Leu Glu Leu Leu Lys Leu His Glu Arg Val Leu Tyr Ile Asp Ile
            180                 185                 190

Asp Ile His His Gly Asp Gly Val Glu Glu Ala Phe Tyr Thr Thr Asn
        195                 200                 205

Arg Val Met Thr Val Ser Phe His Lys Phe Gly Asp Tyr Phe Pro Gly
```

-continued

```
                210                 215                 220
Thr Gly Asp Ile Arg Asp Ile Gly Tyr Ser Glu Gly Lys Tyr Tyr Cys
225                 230                 235                 240

Leu Asn Val Pro Leu Asp Asp Gly Ile Asp Asp Ser Tyr Gln Ser
            245                 250                 255

Ile Phe Lys Pro Ile Ile Ser Lys Val Met Glu Met Tyr Arg Pro Gly
                260                 265                 270

Ala Val Val Leu Gln Cys Gly Ala Asp Ser Leu Ser Gly Asp Arg Leu
                275                 280                 285

Gly Cys Phe Asn Leu Ser Gly Lys Gly His Ala Glu Cys Val Lys Phe
290                 295                 300

Met Arg Ser Phe Asn Val Pro Leu Leu Leu Gly Gly Gly Gly Tyr
305                 310                 315                 320

Thr Ile Arg Asn Val Ala Arg Cys Trp Cys Tyr Glu Thr Gly Val Ala
                325                 330                 335

Leu Gly Glu Glu Leu Gln Glu Lys Leu Pro Tyr Asn Glu Tyr Tyr Glu
                340                 345                 350

Tyr Phe Gly Pro Glu Tyr Ser Leu Tyr Val Ala Ala Ser Asn Met Glu
            355                 360                 365

Asn Arg Asn Thr Asn Lys Gln Leu Glu Glu Ile Lys Cys Asn Ile Leu
370                 375                 380

Asp Asn Leu Ser Lys Leu Gln His Ala Pro Ser Val Gln Phe Gln Glu
385                 390                 395                 400

Arg Ile Pro Glu Thr Lys Leu Pro Glu Pro Asp Glu Asp Gln Glu Asp
                405                 410                 415

Pro Asp Glu Arg His Asp Pro Asp Ser Asp Met Val Leu Asp Asp His
                420                 425                 430

Lys Pro Thr Gly His Ser Ala Arg Ser Leu Ile His Asn Ile Gly Val
            435                 440                 445

Lys Arg Glu Ile Thr Glu Thr Glu Thr Lys Asp Gln His Gly Lys Arg
            450                 455                 460

Leu Thr Thr Glu His Lys Gly Pro Glu Pro Met Ala Glu Asp Leu Gly
465                 470                 475                 480

Ser Ser Lys Gln Ala Pro Thr Ala Asp Ala Asn Ala Val Ala Val Asn
            485                 490                 495

Ala Pro Gly Asn Ala Arg Asn Glu Pro Gly Ser Ser Pro Lys
                500                 505                 510
```

<210> SEQ ID NO 16
<211> LENGTH: 20
<212> TYPE: DNA
<213> ORGANISM: Artificial Sequence
<220> FEATURE:
<223> OTHER INFORMATION: primer P3

<400> SEQUENCE: 16
ggtggtgtct gaatctccta                                              20

<210> SEQ ID NO 17
<211> LENGTH: 20
<212> TYPE: DNA
<213> ORGANISM: Artificial Sequence
<220> FEATURE:
<223> OTHER INFORMATION: primer R3

<400> SEQUENCE: 17
agatggcatc agttactaag                                              20

```
<210> SEQ ID NO 18
<211> LENGTH: 586
<212> TYPE: DNA
<213> ORGANISM: Artificial Sequence
<220> FEATURE:
<223> OTHER INFORMATION: MAR probe b

<400> SEQUENCE: 18
ggatccataa tataactgta ccaggttttg gtttattaca tgtgactgac ggcttcctat        60
gcgtgctcag aaaacggcag ttgggcactg cactgcccgg tgatggtgcc acggtggctc       120
ctgccgcctt ctttgatatt cactctgttg tatttcatct cttgttgccg atgaaaggat       180
ataacagtct ctgaggaaat acttggtatt tcttctgatc agcgttttta taagtaatgt       240
tgaatattgg ataaggctgt gtgtcctttg tcttgggaga caaagcccac agcaggtggt       300
ggttgggtgg tggcagctca gtgacaggag aggttttttt gcctgttttt tttgttgttt       360
ttttttttta agtaaggtgt tcttttttct tagtaaaatt tctactggac tgtatgtttt       420
gacaggtcag aaacatttct tcaaaagaag aacctttgg  aaactgtaca gcccttttct       480
ttcattccct ttttgctttc tgtgccaatg cctttggttc tgattgcatt atggaaaacg       540
ttgatcggaa cttgaggttt ttatttatag tgtggcttga aagctt                      586
```